United States Patent
Sato

(10) Patent No.: US 9,924,874 B2
(45) Date of Patent: Mar. 27, 2018

(54) MEASUREMENT DEVICE, MEASUREMENT METHOD, PROGRAM AND RECORDING MEDIUM

(75) Inventor: Hideo Sato, Tokyo (JP)

(73) Assignee: Sony Corporation (JP)

( * ) Notice: Subject to any disclaimer, the term of this patent is extended or adjusted under 35 U.S.C. 154(b) by 334 days.

(21) Appl. No.: 14/356,742

(22) PCT Filed: Sep. 7, 2012

(86) PCT No.: PCT/JP2012/072894
§ 371 (c)(1),
(2), (4) Date: May 7, 2014

(87) PCT Pub. No.: WO2013/073270
PCT Pub. Date: May 23, 2013

(65) Prior Publication Data
US 2014/0316224 A1    Oct. 23, 2014

(30) Foreign Application Priority Data
Nov. 16, 2011   (JP) ................. 2011-250998

(51) Int. Cl.
*A61B 5/1455*   (2006.01)
*A61B 5/00*     (2006.01)
*A61B 5/145*    (2006.01)

(52) U.S. Cl.
CPC .......... *A61B 5/0077* (2013.01); *A61B 5/0075* (2013.01); *A61B 5/1455* (2013.01);
(Continued)

(58) Field of Classification Search
CPC ....... A61B 5/1455; A61B 5/68; A61B 5/6801; A61B 5/72
See application file for complete search history.

(56) References Cited

U.S. PATENT DOCUMENTS

| 5,529,065 A * | 6/1996 | Tsuchiya .............. A61B 5/0059 600/310 |
| 6,353,226 B1 | 3/2002 | Khalil et al. |

(Continued)

FOREIGN PATENT DOCUMENTS

| JP | 2003-510556 A | 3/2003 |
| JP | 2006-122579 A | 5/2006 |

(Continued)

OTHER PUBLICATIONS

International Search Report dated Oct. 16, 2012.

*Primary Examiner* — Eric Winakur
(74) *Attorney, Agent, or Firm* — Lerner, David, Littenberg, Krumholz & Mentlik, LLP

(57) ABSTRACT

A measurement device according to the present disclosure includes a light source for emitting measurement light which is used for measuring an in vivo component present in a living body and belongs to a predetermined wavelength band toward the living body, a detection unit in which a plurality of sensors is regularly arranged in a predetermined arrangement and which detects the measurement light emitted from the light source and passing through the living body with the plurality of sensors, and an analysis unit which analyzes an amount of the in vivo component based on an amount of light attenuated depending on an optical distance from the light source by use of a detection result detected by the detection unit.

8 Claims, 10 Drawing Sheets

(52) U.S. Cl.
CPC .............. *A61B 5/443* (2013.01); *A61B 5/72* (2013.01); *A61B 5/14532* (2013.01); *A61B 5/14542* (2013.01)

(56) References Cited

U.S. PATENT DOCUMENTS

| | | | |
|---|---|---|---|
| 6,615,061 | B1 | 9/2003 | Khalil et al. |
| 6,630,673 | B2 | 10/2003 | Khalil et al. |
| 7,248,907 | B2 | 7/2007 | Hogan |
| 8,200,306 | B2 | 6/2012 | Hogan et al. |
| 2009/0326347 | A1* | 12/2009 | Scharf .............. A61B 5/14552 600/323 |

FOREIGN PATENT DOCUMENTS

| | | |
|---|---|---|
| JP | 2008-517664 A | 5/2008 |
| WO | 98-0023916 A1 | 6/1998 |

\* cited by examiner

FIG. 1
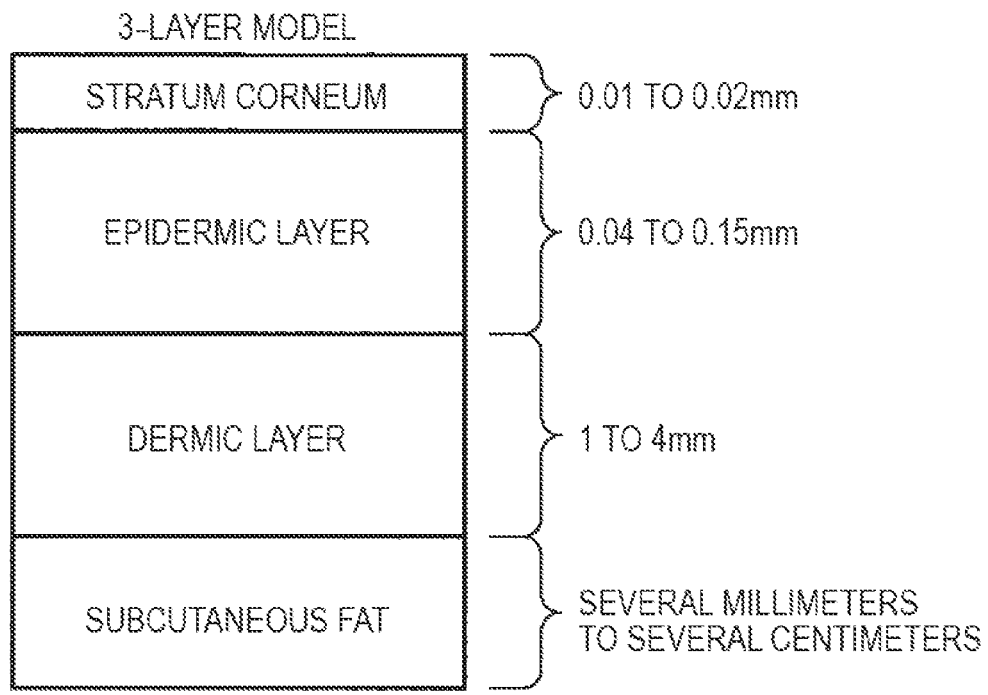
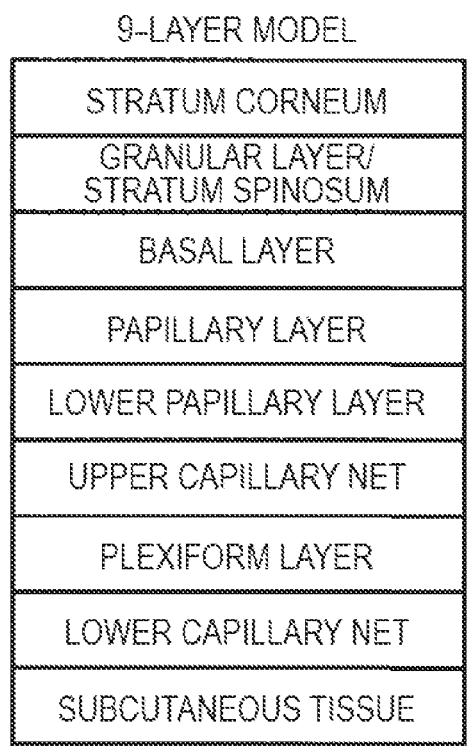

$$A(\lambda) = \sum_i A_i(\lambda) + G(\lambda) = \sum_i \varepsilon_i(\lambda) C_i l_i(\lambda) + G(\lambda)$$

$$A_i(\lambda) = \sum_j \varepsilon_{ij}(\lambda) C_{ij} l_i(\lambda)$$

MEASUREMENT DEVICE, MEASUREMENT METHOD, PROGRAM AND RECORDING MEDIUM

CROSS-REFERENCE TO RELATED APPLICATION

The present application is a national phase entry under 35 U.S.C. § 371 of International Application No. PCT/JP2012/072894 filed Sep. 7, 2012, published on May 23, 2013 as WO 2013/073270 A1, which claims priority from Japanese Patent Application No. JP 2011-250998 filed in the Japanese Patent Office on Nov. 16, 2011.

TECHNICAL FIELD

The present disclosure relates to a measurement device, a measurement method, a program, and a recording medium.

BACKGROUND ART

There are progressively done researches on a technique for non-invasively measuring substances subcutaneously present in a living body by use of various electromagnetic waves or ultrasonic waves such as ultraviolet shine and millimeter wave. For example, the following Patent Literature 1 discloses therein a method and device for non-invasively measuring a blood glucose level by use of a near-infrared light.

CITATION LIST

Patent Literature

Patent Literature 1: JP 2006-122579A

SUMMARY OF INVENTION

Technical Problem

With the body measurement technique using non-invasive optical measurement as described in Patent Literature 1 or the like described above, however, an effect caused by a constitutional difference or the like of each person remarkably hinders a measurement accuracy. For example, with a device for measuring glucose, albumin, AGEs (Advanced Glycation Endproducts) and the like in a body by use of spectroscopy such as Raman spectroscopy or near-infrared spectroscopy, fluorescent analysis using ultraviolet ray excitation, or the like, an over-time change of a person to be measured, obesity, suntan, racial difference, constitutional difference, or the like causes an error on optical measurement. The optical measurement of glucose, AGEs or the like is generally a multivariate analysis, and does not meet a variation in optical model.

Thus, if the amount of varied component for an error factor caused by a person to be measured can be specified prior to measuring a body substance of interest, a variation in optical mode can be estimated, thereby enhancing reliability of the body measurement technique.

There is therefore proposed, in the present disclosure, a measurement device, a measurement method, a program and a recording medium capable of accurately measuring an in vivo component which can cause a variation in optical model in terms of the above problems.

Solution to Problem

According to the present disclosure, there is provided a measurement device including a light source for emitting measurement light which is used for measuring an in vivo component present in a living body and belongs to a predetermined wavelength band toward the living body, a detection unit in which a plurality of sensors is regularly arranged in a predetermined arrangement and which detects the measurement light emitted from the light source and passing through the living body with the plurality of sensors, and an analysis unit which analyzes an amount of the in vivo component based on an amount of light attenuated depending on an optical distance from the light source by use of a detection result detected by the detection unit.

Further, according to the present disclosure, there is provided a measurement method including emitting measurement light which is used for measuring an in vivo component present in a living body and belongs to a predetermined wavelength band toward the living body, detecting the measurement light passing through the living body with a detection unit in which a plurality of sensors is regularly arranged in a predetermined arrangement, and analyzing an amount of the in vivo component based on an amount of light attenuated depending on an optical distance from a light source of the measurement light by use of a detected detection result.

Further, according to the present disclosure, there is provided a program for causing a computer capable of controlling a measurement device including a light source for emitting measurement light which is used for measuring an in vivo component present in a living body and belongs to a predetermined wavelength band toward the living body, and a detection unit in which a plurality of sensors is regularly arranged in a predetermined arrangement and which detects the measurement light emitted from the light source and passing through the living body with the plurality of sensors to achieve a control function of controlling the light source and the detection unit, and an analysis function of analyzing an amount of the in vivo component based on an amount of light attenuated depending on an optical distance from the light source by use of a detection result detected by the detection unit.

Further, according to the present disclosure, there is provided a recording medium recording a program therein, the program causing a computer capable of controlling a measurement device including a light source for emitting measurement light which is used for measuring an in vivo component present in a living body and belongs to a predetermined wavelength band toward the living body, and a detection unit in which a plurality of sensors is regularly arranged in a predetermined arrangement and which detects the measurement light emitted from the light source and passing through the living body with the plurality of sensors to achieve a control function of controlling the light source and the detection unit, and an analysis function of analyzing an amount of the in vivo component based on an amount of light attenuated depending on an optical distance from the light source by use of a detection result detected by the detection unit.

Further, according to the present disclosure, there is provided a measurement device including a body substance measurement device which measures a substance to be measured contained in a living body, a light source for emitting measurement light which is used for measuring a different in vivo component from the substance to be measured present in the living body and belongs to a predetermined wavelength band toward the living body, a detection unit in which a plurality of sensors is regularly arranged in a predetermined arrangement and which detects the measurement light emitted from the light source and passing through the living body with the plurality of sensors, and an analysis unit which analyzes an amount of the in vivo component based on an amount of light attenuated depending on an optical distance from the light source by use of a detection result detected by the detection unit.

Further, according to the present disclosure, there is provided a measurement device including a body substance measurement device which measures a substance to be measured contained in a living body, a light source for emitting measurement light which is used for measuring a different in vivo component from the substance to be measured present in the living body and belongs to a predetermined wavelength band toward the living body, a detection unit in which a plurality of sensors is regularly arranged in a predetermined arrangement and which detects the measurement light emitted from the light source and passing through the living body with the plurality of sensors, and an analysis unit which analyzes an amount of the in vivo component based on an amount of light attenuated depending on an optical distance from the light source by use of a detection result detected by the detection unit. The body substance measurement device or the analysis unit corrects a measurement result in the body substance measurement device by use of the amount of the in vivo component.

According to the present disclosure, the light source emits measurement light which is used for measuring an in vivo component present in a living body and belongs to a predetermined wavelength band toward the living body, the detection unit in which a plurality of sensors is regularly arranged in a predetermined arrangement detects the measurement light emitted from the light source and passing through the living body, and the analysis unit uses a detection result detected by the detection unit to analyze the amount of in vivo component based on the amount of light attenuated depending on an optical distance from the light source.

Advantageous Effects of Invention

According to the present disclosure as described above, it is possible to accurately measure an in vivo component which can cause a variation in optical model.

BRIEF DESCRIPTION OF DRAWINGS

FIG. 1 is an explanatory diagram illustrating an exemplary human body's skin structure model.

DESCRIPTION OF EMBODIMENTS

Figure 2:
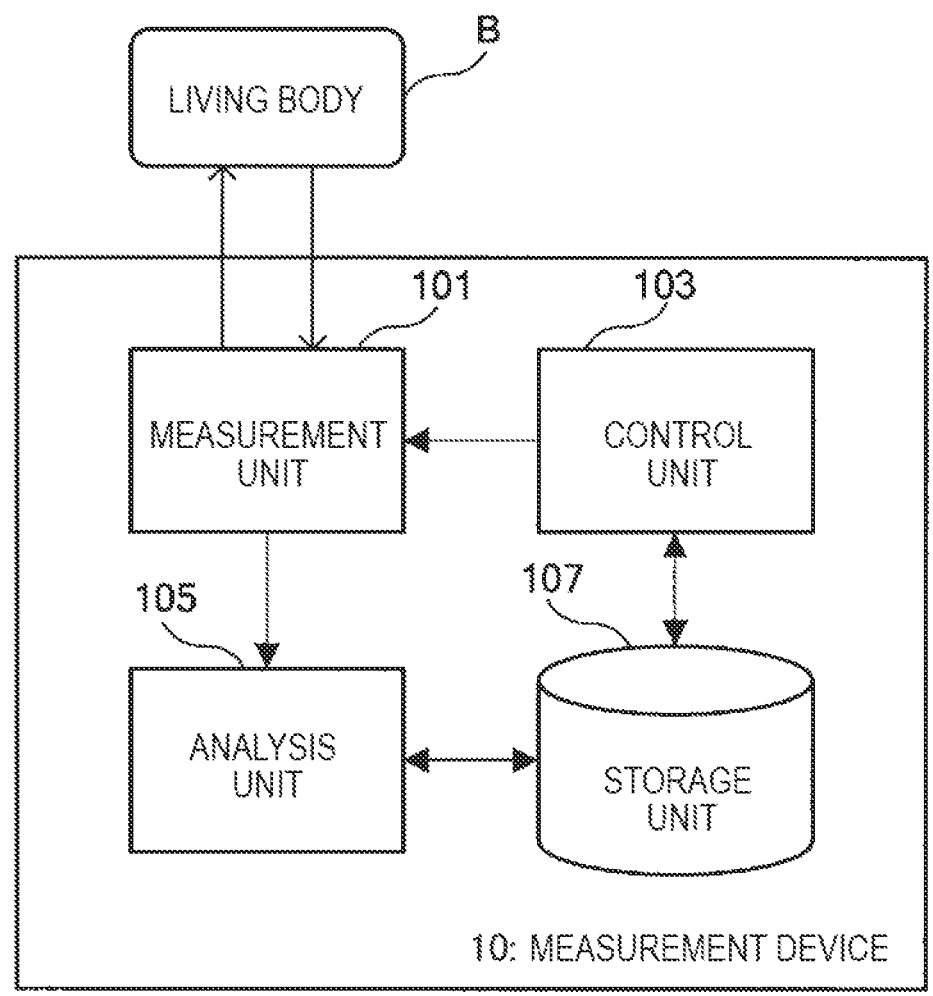
FIG. 2 is a block diagram illustrating a structure of a measurement device according to a first embodiment of the present disclosure.

Hereinafter, preferred embodiment of the present disclosure will be described in detail with reference to the appended drawings. Note that, in this specification and the drawings, elements that have substantially the same function and structure are denoted with the same reference signs, and repeated explanation is omitted.

The explanation will be made in the following order.
(1) Human body's skin structure model
(2) First embodiment
(2-1) Structure of measurement device
(2-2) Variants
(3) Hardware structure of measurement device according to embodiment of present disclosure
(4) Conclusion
(Human Body's Skin Structure Model)

A skin structure model as a modeled human body's skin structure will be briefly described with reference to FIG. 1 prior to describing a measurement device, a measurement method and a program according to an embodiment of the present disclosure. FIG. 1 is an explanatory diagram illustrating an exemplary human body's skin structure model.

In recent years, there has been developed a technique for measuring components in the blood or fluid such as glucose, albumin, AGEs (Advanced Glycation Endproducts), cholesterol and oxygenated/reduction hemoglobin, melanin, fat, and the like present in a living body with non-invasive optical measurement. Such a body measurement technique is accomplished by using spectroscopy such as Raman spectroscopy or near-infrared spectroscopy, measuring a change in refractive index, using various electromagnetic waves such as ultraviolet shine and millimeter waves, or using ultrasonic waves, and multivariate analysis is mainly used for analyzing measured data.

How a human body's skin structure is modeled is important for analyzing measured data. An exemplary human body's skin structure model is a 3-layer model or 9-layer model as illustrated in FIG. 1.

The 3-layer model illustrated in FIG. 1 is such that subcutaneous tissues below the stratum corneum of the skin are modelled into the three layers of epidermic layer, dermic layer and subcutaneous fat. In the 3-layer model, though depending on a person, the stratum corneum is equivalent to about 0.01 to 0.02 mm inward from the body surface, the epidermic layer is equivalent to about 0.04 to 0.15 mm from the body surface, the dermic layer is equivalent to about 1 to 4 mm from the body surface, and the subcutaneous fat is equivalent to about several millimeters to several centimeters from the body surface.

The 9-layer model illustrated in FIG. 1 is such that the human body's skin structure is divided in more details and the human body's skin structure is modeled to be configured of nine layers from the stratum corneum to the subcutaneous tissues.

In the skin structure, melanin as a component in the body is mainly present in the epidermic layer, and may be possibly present in the basal layer. Capillaries are present in the dermic layer in the 3-layer model, and various blood components such as oxygenated hemoglobin and reduction hemoglobin are present inside the capillaries. Fat cells are mainly present in the subcutaneous fat in the 3-layer model or in the subcutaneous tissues in the 9-layer model. Therefore, a skin structure model to be taken into consideration is important for measuring the above components with non-invasive optical measurement.

However, the human body's skin structure, or various components contained in the skin structure vary depending on an over-time change of a person to be measured, obesity, suntan, racial difference, sex, constitution, and the like, and largely depends on personal characteristics. The positions of capillaries and the like are known as slightly changing due to bathing in hot water. Thus, non-invasive measurement of a component in the body based on the skin structure model is strongly influenced by a variation in the skin structure model illustrated in FIG. 1.

However, the method for non-invasively measuring an in vivo substance currently proposed does not take into consideration a variation in the skin structure model, and an error caused by the variation described above may be overlapped on a measurement result. Therefore, the present inventors have eagerly studied a technique capable of correcting an effect on a measurement result caused by a constitutional difference of a person to be measured in terms of the above circumstances. Consequently, the present inventors have achieved a measurement device and method according to an embodiment of the present disclosure described below.

(First Embodiment)
<Structure of Measurement Device>

Figure 3:
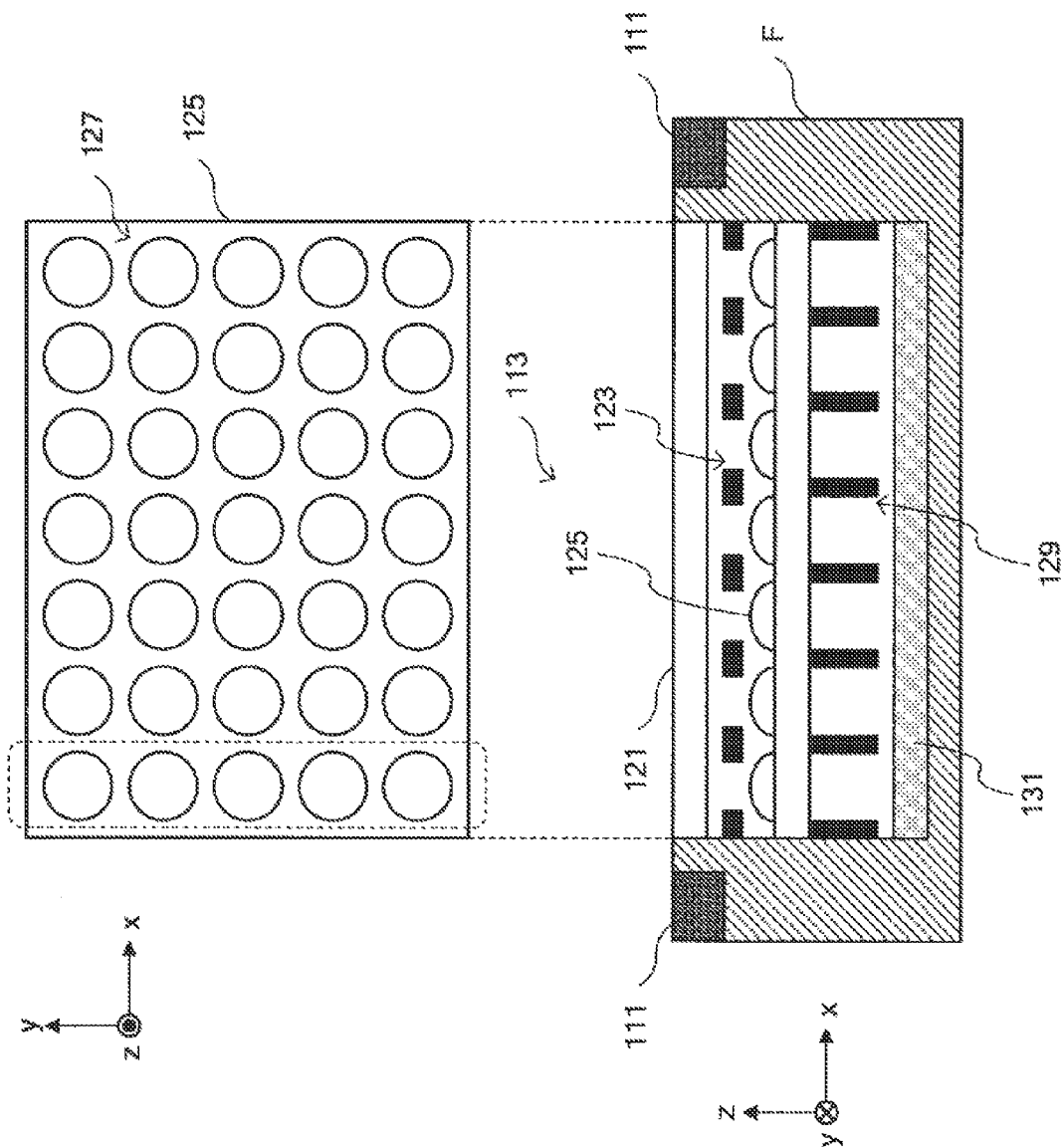
FIG. 3 is an explanatory diagram illustrating an exemplary measurement unit provided in the measurement device according to the embodiment.
Figure 4:
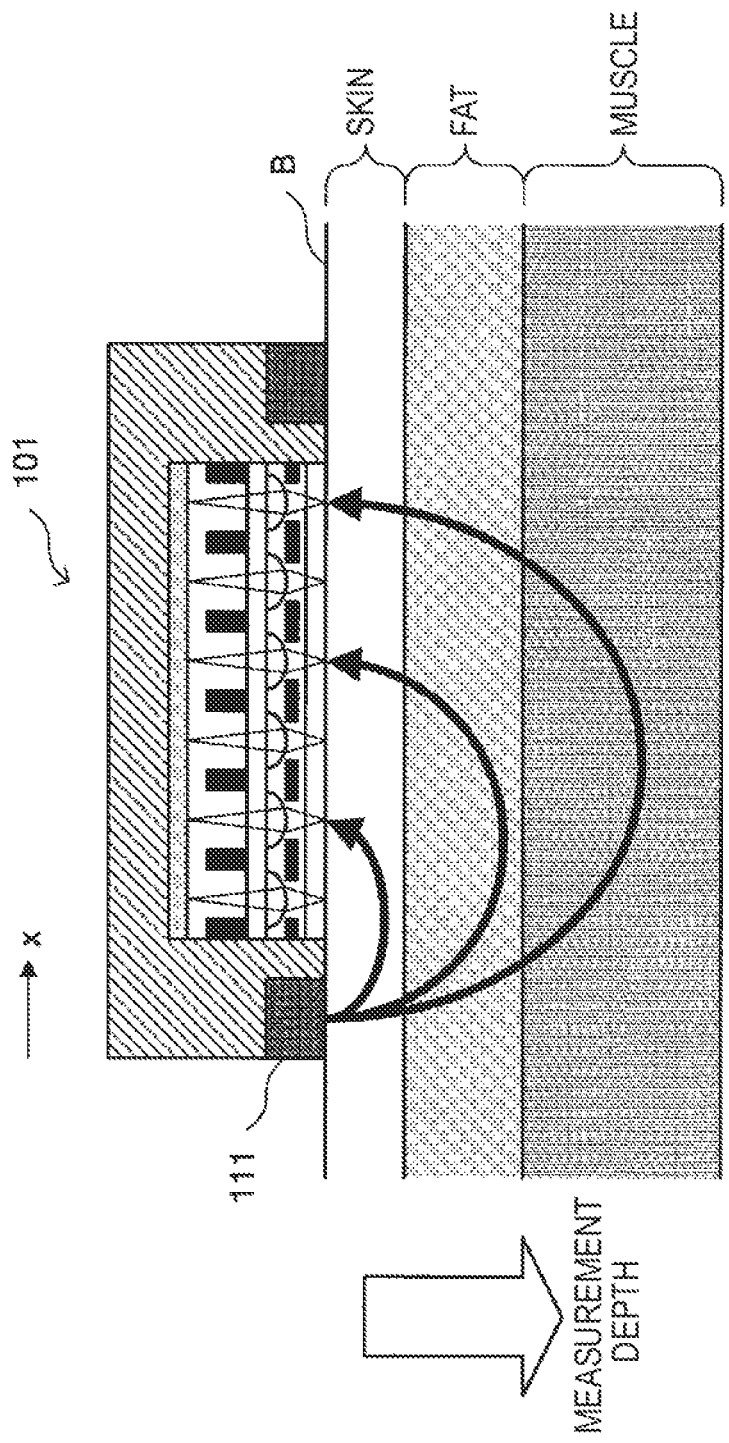
FIG. 4 is an explanatory diagram for explaining the measurement device according to the embodiment.
Figure 5:
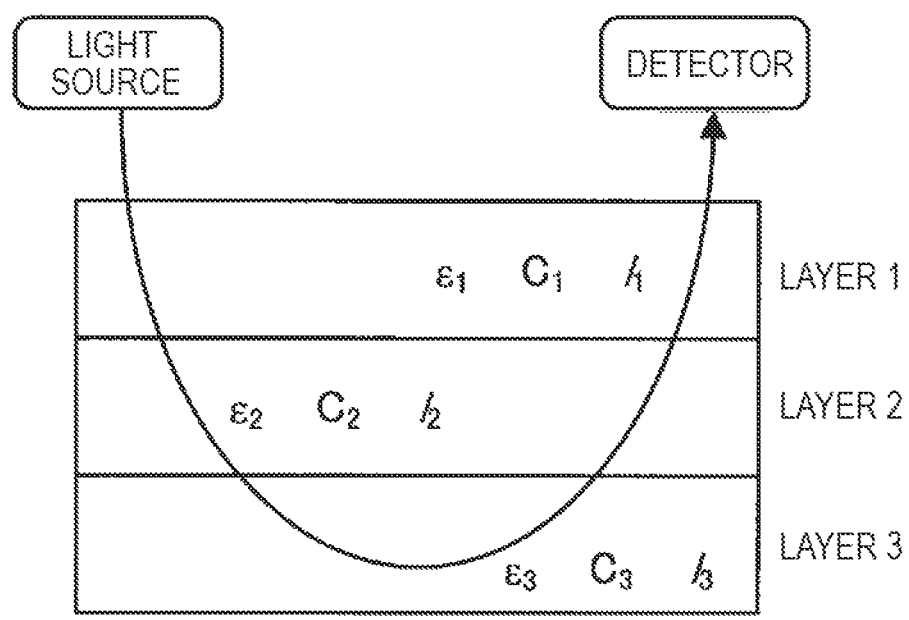
FIG. 5 is an explanatory diagram for explaining the extended Lambert-Beer Law.
Figure 6A:
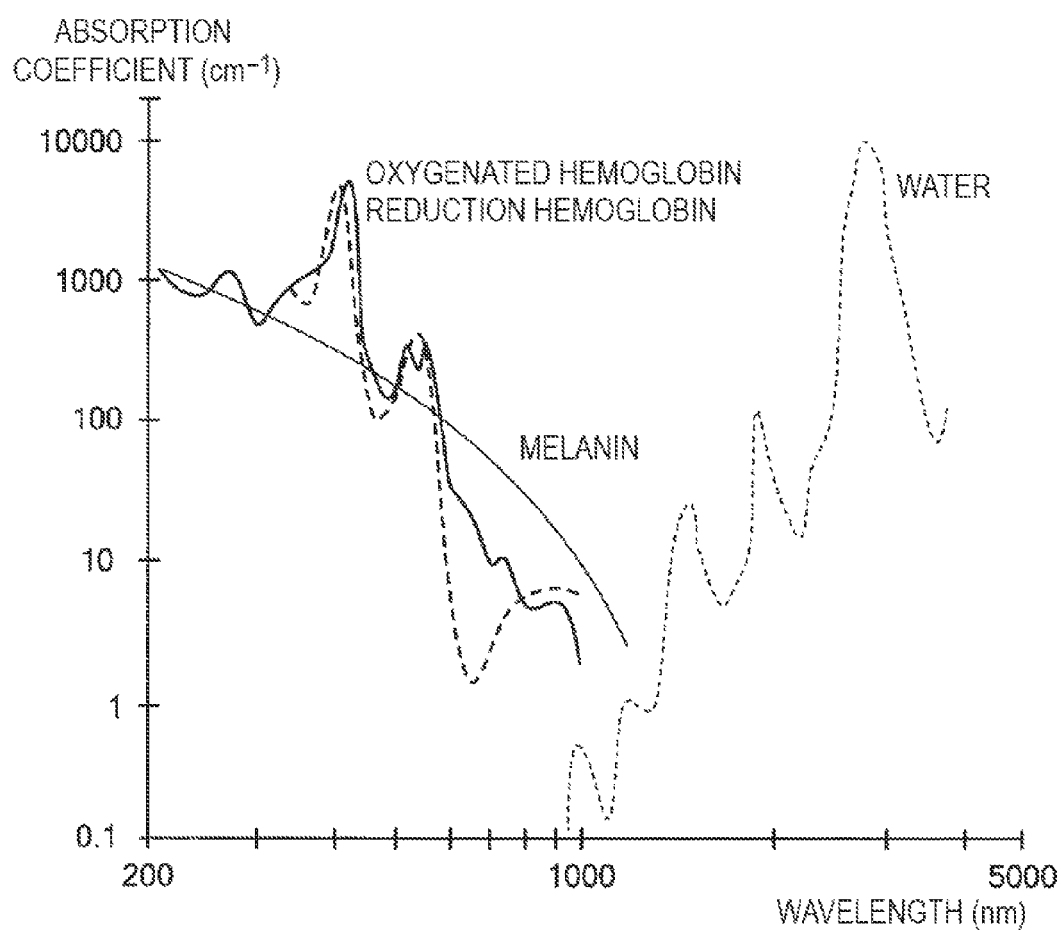
FIG. 6A is a graph illustrating exemplary photoabsorption spectra of in vivo components.
Figure 6B:
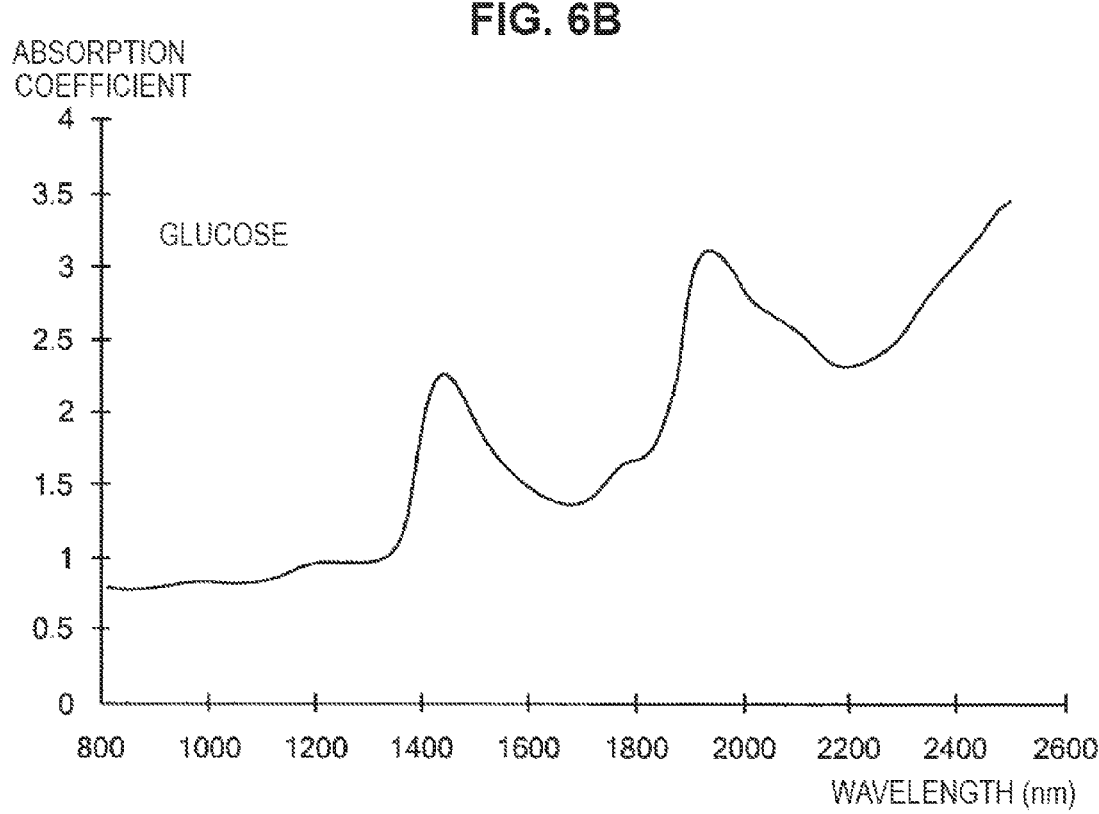
FIG. 6B is a graph illustrating an exemplary photoabsorption spectrum of an in vivo component.
Figure 6C:
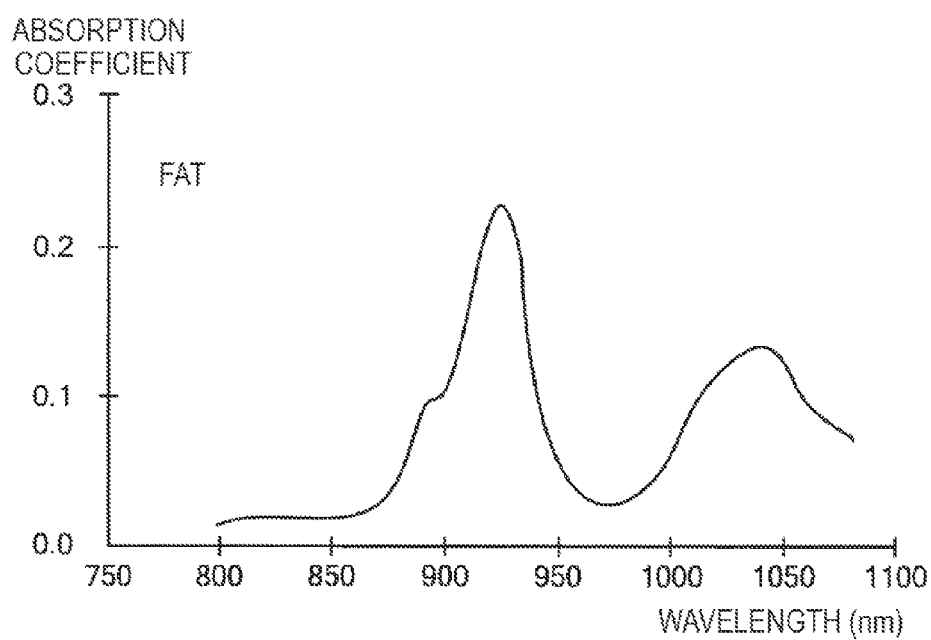
FIG. 6C is a graph illustrating an exemplary photoabsorption spectrum of an in vivo component.
Figure 7:
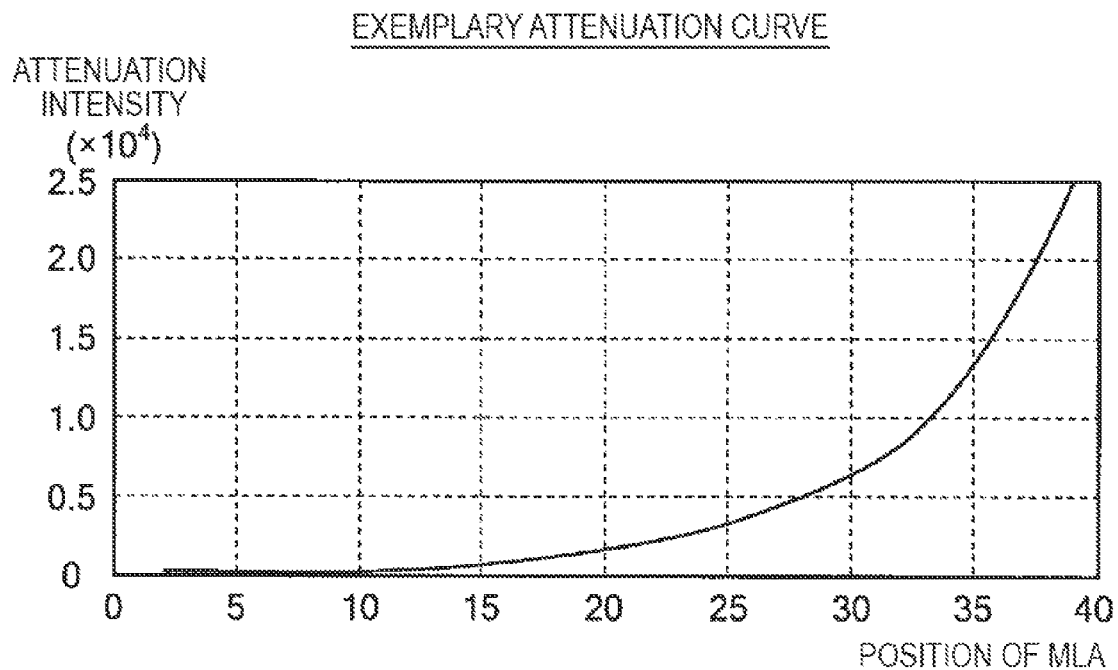
FIG. 7 is a graph illustrating an exemplary attenuation curve used in the measurement device according to the embodiment.

Subsequently, a measurement device and a measurement method according to a first embodiment of the present disclosure will be described in detail with reference to FIG. 2 to FIG. 7. FIG. 2 is a block diagram illustrating a structure of a measurement device 10 according to the present embodiment. FIG. 3 is an explanatory diagram illustrating an exemplary measurement unit provided in the measurement device 10 according to the present embodiment. FIG. 4 is an explanatory diagram for explaining the measurement device 10 according to the present embodiment. FIG. 5 is an explanatory diagram for explaining the extended Lambert-Beer Law. FIGS. 6A to 6C are the graphs illustrating exemplary photoabsorption spectra of in vivo components. FIG. 7 is a graph illustrating an exemplary attenuation curve used in the measurement device 10 according to the present embodiment.

An entire structure of the measurement device 10 according to the present embodiment will be first described in detail with reference to FIG. 2.

The measurement device 10 according to the present embodiment is directed for measuring a living body B to be measured by use of light with a predetermined wavelength, and calculating the amount of in vivo component contained in the living body B based on a resultant measurement result. The measurement device 10 can generate an attenuation curve indicating how an irradiated light attenuates due to the in vivo component inside the living body B based on the measurement result of the amount of component.

The measurement device 10 mainly includes a measurement unit 101 for measuring the living body B, a control unit 103, an analysis unit 105 and a storage unit 107 as illustrated in FIG. 2.

[Measurement Unit 101]

At first, a structure of the measurement unit 101 according to the present embodiment will be specifically described with reference to FIG. 3 and FIG. 4.

The measurement unit 101 according to the present embodiment is configured of a light source 111 and a detection unit 113 as illustrated in FIG. 3.

Light Source

The light source 111 emits measurement light which is used for measuring an in vivo component present in a living body and belongs to a predetermined wavelength band toward the living body B. The light source 111 is arranged in a predetermined frame F such that the emission face of measurement light opposes the living body B. The light source 111 emits light with a suitable wavelength for measuring an in vivo component of interest in the measurement device 10 according to the present embodiment, and can emit one or plural kinds of light.

A wavelength of measurement light emitted from the light source 111 can be appropriately set depending on an in vivo component of interest. The light source 111 emits light with a wavelength of 940 nm or 950 nm so that fat present in the subcutaneous tissues can be known. The light source 111 emits light with a wavelength of 568 nm, 580 nm, 660 nm or 890 nm so that components in the blood such as oxygenated/reduction hemoglobin, or melanin pigment can be known. Further, the light source 111 emits light with a wavelength of 1400 nm to 2200 nm so that glucose can be known. The light with a plurality of wavelengths is emitted from the light source 111 in a time division manner, for example.

Various wavelengths described above are merely exemplary, and the light emitted from the light source 111 in the measurement device 10 according to the present embodiment is not limited to the above examples.

The light source 111 may use a light emitting diode (LED), a small-sized laser, or the like, for example, and one or a plurality of such light emitting devices are provided for the light source 111.

The light source 111 is controlled by the control unit 103 described later in terms of an emission timing of the measurement light, an intensity of measurement light to be emitted, and the like.

A shape of the frame F in which the light source 111 is arranged is not particularly limited, but a wall as illustrated in FIG. 3 is provided between the light source 111 and the detection unit 113 described later so that the wall can be employed as a light shielding wall for preventing light emitted from the light source 111 from entering the detection unit 113.

Detection Unit

The detection unit 113 provided in the measurement device 10 according to the present embodiment regularly arranges a plurality of sensors in a predetermined arrangement therein, and is directed for detecting measurement light emitted from the light source 111 and passing through the living body B with the sensors. In other words, the detection unit 113 according to the present embodiment is configured of a so-called multi-tap sensor. FIG. 3 illustrates a sensor utilizing a micro lens array (MLA) as an exemplary detection unit 113.

The detection unit 113 provided in the measurement device 10 according to the present embodiment mainly includes a transparent substrate 121 capable of transmitting light with a wavelength band to which measurement light emitted from the light source 111 belongs, a first light shield 123, a micro lens array 125, a second light shield 129, and a sensor 131, for example, as illustrated in FIG. 3.

The transparent substrate 121 is where part of the living body B to be measured is arranged. The transparent substrate 121 is formed of a substrate capable of transmitting light with a wavelength used in the measurement processing. When measurement light emitted from the light source 111 and passing inside the living body B passes through the transparent substrate 121, its directivity is controlled by the first light shield 123.

The first light shield 123 functions as a directivity control plate for controlling directivity of measurement light passing through the transparent substrate 121, and is provided at a boundary between mutually adjacent micro lenses 127 in the micro lens array 125 described later. The first light shield 123 is provided so that directivity of measurement light incident into each micro lens 127 can be controlled, which enables more accurate measurement. The measurement light passing through the first light shield 123 is guided to the micro lens array 125.

The micro lens array 125 is configured of a plurality of micro lenses 127 as light receiving lenses as illustrated in the upper part of FIG. 3, and each micro lens 127 is arranged in the x direction and in the y direction on a predetermined substrate in a grid shape. Each micro lens 127 guides measurement light incident into the micro lens 127 to the sensor 131 described later. The micro lens array 125 has less curvature of field and has no distortion in the depth direction. Such a micro lens array 125 is used thereby to acquire better measurement data. A depth of field of each micro lens 127 configuring the micro lens array 125 is set to cover the skin structure of interest (to focus up to a depth of 10 mm from the body surface, for example) by the measurement device 10 according to the present embodiment.

The number of micro lenses 127 arranged in the micro lens array 125 according to the present embodiment is not limited to the example illustrated in the upper part of FIG. 3. The number of micro lenses 127 arranged in the micro lens array 125 according to the present embodiment can be freely set depending on a size of a living body to be shot or a size of the sensor 131.

Measurement light incident into the micro lens array 125 is focused into the micro lenses 127 to be image-formed to the sensor 131 described later.

Herein, the second light shield 129 is provided at a boundary between mutually adjacent micro lenses 127 at the face of the micro lens array 125 on the sensor 131 side. The second light shield 129 enables directivity of measurement light passing through the micro lens array 125 to be controlled, and enables light incident into each micro lens 127 to be separated from light incident into an adjacent micro lens 127. Thereby, the measurement device 10 according to the present embodiment can select measurement light focused into the sensor 131.

The sensor 131 detects an intensity of measurement light at each position in the xy plane illustrated in the upper part of FIG. 3. The sensor 131 converts an intensity of measurement light received by a photo detector (PD) or the like into an electric signal to be output to the analysis unit 105 described later. The sensor 131 may employ a 2D area sensor such as photodiode, CCD (Charge Coupled Devices) image sensor, CMOS (Complementary Metal Oxide Semiconductor) image sensor, sensor using organic EL as light receiving device, or TFT (Thin Film Transistor) image sensor. A 1D sensor such as line sensor in the x axis direction may be mounted as a simplified model on the sensor.

The sensor 131 is controlled by the control unit 103 described later in terms of scan timing and the like, and can output a detection intensity at any position in the upper part of FIG. 3 to the analysis unit 105, for example.

The structure of the measurement unit 101 according to the present embodiment has been described above in detail with reference to FIG. 3.

Data to be Measured by Measurement Unit

Data (measurement data) to be measured by the measurement unit 101 according to the present embodiment will be described below in detail with reference to FIG. 4.

A human body is a medium which excellently scatters light, and thus measurement light emitted from the light source 111 and incident into the living body B travels while scattering inside the living body B, and is detected by the detection unit provided at any position. At this time, as schematically illustrated in FIG. 4, the detection unit farther away from the light source 111 can detect measurement light which scatters deeper and returns to the body surface. That is, in FIG. 4, a sensor farther away from the light source 111 in the x axis direction (sensor positioned on the right side in FIG. 4, for example) can detect a deeper-penetrated measurement light.

Energy in a specific wavelength of measurement light is absorbed depending on a length of a distance (optical distance) in which the light travels due to various in vivo components present in the optical path, and its intensity attenuates. Thus, in the schematic diagram illustrated in FIG. 4, for example, energy of measurement light focused by the second micro lens array from the left and detected by the sensor is absorbed due to various in vivo components present in the cutaneous layer illustrated in FIG. 4, and its intensity attenuates. Thus, measurement light detected by the sensor corresponding to the position may be measurement data including the knowledge on the cutaneous layer illustrated in FIG. 4. Similarly, in the schematic diagram illustrated in FIG. 4, energy of measurement light focused by the third micro lens array from the right and detected by the sensor is absorbed due to various in vivo components present in the cutaneous layer and the fat layer illustrated in FIG. 4, and its intensity attenuates. Thus, measurement light detected by the sensor corresponding to the position may be measurement data including the knowledge on the cutaneous layer and the fat layer illustrated in FIG. 4. Further, in the schematic diagram illustrated in FIG. 4, energy of measurement light focused by the rightmost micro lens array and detected by the sensor is absorbed due to various in vivo components present in the cutaneous layer, the fat layer and the muscular layer illustrated in FIG. 4, and its intensity attenuates. Thus, measurement light detected by the sensor corresponding to the position may be measurement data including the knowledge on the cutaneous layer, the fat layer and the muscular layer illustrated in FIG. 4.

The measurement device 10 according to the present embodiment uses the output (measurement data) from a sensor positioned at a different x coordinate indicated in FIG. 4 thereby to model the characteristics of scattering or attenuating of the light at each sensor position based on the characteristics of the light.

[Control Unit 103]

Returning to FIG. 2, the control unit 103 provided in the measurement device 10 according to the present embodiment will be described.

The control unit 103 is realized by CPU (Central Processing Unit), ROM (Read Only Memory), RAM (Random Access Memory), or the like, for example. The control unit 103 controls to drive the light source 111, the sensor 131 and the like provided in the measurement unit 101, thereby governing the total measurement processing on the living body B in the measurement unit 101. More specifically, the control unit 103 controls the driving of the sensor such as scan timing of the sensor 131 or selection of the sensor 131 for acquiring information based on a predetermined synchronization signal or the like. Further, the control unit 103 controls the driving of the light source 111 for emission timing or intensity of measurement light.

The control unit 103 controls the above driving so that the light source 111 of the measurement unit 101 can emit measurement light with a different wavelength in a time division manner and can acquire measurement data at any position on the sensor 131 in a time division manner.

Measurement data measured by the measurement unit 101 the driving of which is controlled by the control unit 103 is output to the analysis unit 105 described later, where the measurement data is analyzed.

Herein, when controlling the measurement unit 101, the control unit 103 can refer to various programs, parameters, databases and the like recorded in the storage unit 107 described later.

[Analysis Unit 105]

The analysis unit 105 provided in the measurement device 10 according to the present embodiment is realized by CPU, ROM, RAM or the like, for example. The analysis unit 105 uses measurement data detected by the measurement unit 101 and indicating a measurement light detection result to analyze the amount of in vivo component based on the amount of light attenuated depending on an optical distance from the light source.

More specifically, the analysis unit 105 makes multiple regression analysis on actually-measured measurement data by modeling the subcutaneous tissues in the living body and handling "the measurement data measured by the measurement unit 101 as being expressed as a linear sum of absorption of an in vivo component of interest." The analysis unit 105 makes the multiple regression analysis thereby to calculate the amount of in vivo component of interest.

An analysis processing performed by the analysis unit 105 according to the present embodiment will be specifically described below with reference to FIG. 5 to FIG. 7.

The analysis unit 105 uses the extended Lambert-Beer Law to associate actually measured data with the amount of photoabsorption caused by an in vivo component of interest. The measurement device 10 according to the present embodiment focuses a living body, which is an object for scattering light, and takes into consideration propagation of light in the living body, and thus cannot utilize the general Lambert-Beer law which cannot take into consideration a scattering/diffusion effect. Therefore, the analysis unit 105 according to the present embodiment analyzes resultant measurement data by use of the extended Lambert-Beer Law described later. The extended Lambert-Beer Law will be briefly described below with reference to FIG. 5.

The following Equation 101 formulates a rate of light absorbed by a substance present inside a scattering body when light propagates inside the light scattering body such as living body, and is called extended Lambert-Beer Law.

[Math. 1]

$$A(\lambda) = -\log\frac{I(\lambda)}{I_0(\lambda)} \quad \text{(Equation 101)}$$

$$= \sum_i A_i(\lambda) + G(\lambda)$$

$$= \sum_i \varepsilon_i(\lambda)C_i l_i(\lambda) + G(\lambda)$$

where, in the above Equation 101, $\lambda$: Wavelength of light of interest, $A(\lambda)$: Degree of photoabsorption with wavelength $\lambda$, $I_0(\lambda)$: Intensity of light with wavelength $\lambda$ incident into scattering body, $I(\lambda)$: Detection intensity of light with wavelength $\lambda$ passing through scattering body, $G(\lambda)$: Amount of attenuation due to scattering of light with wavelength $\lambda$, and $\varepsilon_i(\lambda)$: Photoabsorption coefficient of light with wavelength $\lambda$ in substance i, which is specific to substance.

$C_i$: Concentration of substance i, and $l_i$: Average optical path length when light with wavelength $\lambda$ propagates in substance i.

The extended Lambert-Beer Law is assumed to be applied to a scattering body having a layer structure as illustrated in FIG. 5. In the following, a subscript for specifying a layer is described as i, and the number of substances contained in the layer i is indicated with a subscript j. The extended Lambert-Beer Law in a scattering body having the layer structure as illustrated in FIG. 5 may be expressed in the following Equation 102 and Equation 103.

[Math. 2]

$$A(\lambda) = -\log\frac{I(\lambda)}{I_0(\lambda)} \quad \text{(Equation 102)}$$

$$= \sum_i A_i(\lambda) + G(\lambda)$$

$$= \sum_i \varepsilon_i(\lambda)C_i l_i(\lambda) + G(\lambda)$$

$$A(\lambda) = \sum_j \varepsilon_{ij}(\lambda)C_{ij}l_i(\lambda) \quad \text{(Equation 103)}$$

where, in the Equation 102 and Equation 103, $\lambda$: Wavelength of light of interest, $A(\lambda)$: Degree of photoabsorption with wavelength $\lambda$, $I_0(\lambda)$: Intensity of light with wavelength $\lambda$ incident into scattering body, $I(\lambda)$: Detection intensity of light with wavelength $\lambda$ passing through scattering body, $G(\lambda)$: Amount of attenuation due to scattering of light with wavelength $\lambda$, $\varepsilon_i(\lambda)$: Photoabsorption coefficient of light with wavelength $\lambda$ in layer i, $C_i$: Concentration of substance contained in layer i, $l_i$: Average optical path length when light with wavelength $\lambda$ propagates in layer i, $\varepsilon_{ij}(\lambda)$: Photoabsorption coefficient of light with wavelength $\lambda$ in substance j contained in layer i, and $C_{ij}$: Concentration of substance j contained in layer i.

Herein, as FIGS. 6A to 6C, a photoabsorption coefficient of an in vivo component of interest can be specified by previously measuring an absorption spectrum of the in vivo component of interest or acquiring data from a well-known database. The spectra indicated in FIG. 6A indicate the wavelength dependency of the absorption coefficients $\varepsilon$ of oxygenated hemoglobin, reduction hemoglobin, melanin and water, FIG. 6B indicates a spectrum indicating wavelength dependency of the absorption coefficient $\varepsilon$ of glucose, and FIG. 6C indicates a spectrum indicating wavelength dependency of the absorption coefficient $\varepsilon$ of fat. Therefore, the photoabsorption coefficient of an in vivo component of interest can be handled as the known amount by use of the data.

The leftmost side in the Equation 102 is actual measurement data on each wavelength which is measured by the measurement unit 101 according to the present embodiment. The measurement unit 101 according to the present embodiment uses a so-called multi-tap sensor such as a sensor using the micro lens array illustrated in FIG. 3, thereby acquiring a plurality of items of measurement data at different x direction positions for the same wavelength λ as illustrated in FIG. 4, for example.

The analysis unit 105 can make multiple regression analysis per wavelength based on a plurality of items of actual measurement data at different sensor positions assuming the fitting parameters such as the concentration $C_{ij}$ of an in vivo component of interest and the average optical path length in the Equation 102 and Equation 103. Thereby, the analysis unit 105 estimates each layer of the skin structure model per wavelength at each sensor position, thereby to calculate the amount of in vivo component of interest or to calculate a thickness of the layer.

The analysis unit 105 can calculate the components in the blood such as melanin, oxygenated hemoglobin and reduction hemoglobin, the amount of water, and the like by the above multiple regression analysis. Further, the analysis unit 105 can calculate a thickness of the fat layer, a thickness of the dermic layer, and the like in addition to the amounts of components described above. The in vivo components capable of being analyzed by the analysis unit 105 are not limited to the above, and any in vivo component whose photoabsorption can be measured may be analyzed.

In this way, the analysis unit 105 according to the present embodiment can model the skin structure at each sensor position by performing the above analysis processing per wavelength by use of actual measurement data acquired from the sensor at each x coordinate position indicated in FIG. 4. The analysis unit 105 can acquire an attenuation curve of a light intensity as illustrated in FIG. 7 by plotting a degree of photoabsorption due to an in vivo component at each sensor position. The attenuation curve can be generated per wavelength of measurement light, and a wavelength specific to the absorption of an in vivo component of interest is selected for the wavelength of the measurement light. Therefore, the attenuation curve for light with a wavelength λ is assumed as an attenuation curve indicating a degree of absorption by an in vivo component.

For example, two kinds of measurement light of light with a wavelength of 660 nm and light with a wavelength of 890 nm are used to be irradiated on the living body B in a time division manner and the intensities thereof are detected in a time division manner so that the analysis unit 105 can calculate the amount of melanin contained in the living body. The analysis unit 105 generates the attenuation curves for the two wavelengths thereby to estimate attenuation of light caused by melanin in the light with a wavelength of 660 nm or to estimate attenuation of light caused by melanin in the light with a wavelength of 890 nm. The light with a wavelength of 660 nm is used as measurement light thereby to calculate a thickness of the dermic layer. Further, light with a wavelength of 940 nm is used as measurement light thereby to acquire an attenuation curve for fat. The analysis unit 105 can calculate a thickness of the fat layer by use of the attenuation curve.

The analysis unit 105 separates an effect due to an in vivo component present in the arterial blood from an effect due to an in vivo component present in the venous blood, thereby separating a temporal variation in components present in the arterial blood like the principle of the pulse oximeter. Thereby, a component with less temporal variation can be more accurately analyzed.

When various multi-tap sensors illustrated in FIG. 3 are used for the measurement unit 101, a group of sensors present in the y axis direction are assumed as the sensors having an x coordinate as is clear from the upper part of FIG. 3. Thus, the analysis unit 105 may integrate measurement data acquired from the group of sensors having the same x coordinate to be used as one item of data, or may use measurement data acquired from one sensor in the y axis direction as it is.

The analysis unit 105 can use the thus-calculated amount of component or the thus-generated attenuation curve for correcting a detection intensity of light with each wavelength. The amount of component or attenuation curve is used for correcting a detection intensity of light, thereby compensating for an effect of photoabsorption by an in vivo component. The correction processing will be described below in detail.

The analysis unit 105 can correct or delete data at a singular point present in a range to be measured, for example. Elements which have effects on a measurement result, such as body hair, bruises and moles on the body surface, or arterial and venous vessels, are present in the living body B. In such a site, the measurement result may discontinuously transit between the sensors in the y axis direction illustrated in the upper part of FIG. 3. Thus, the analysis unit 105 can detect such a site as a singular point in terms of the discontinuity of the measurement data. Consequently, a more accurate measurement result can be acquired even if a measurement position is not visually selected or an average value of multiple measurements is not acquired. Further, the analysis unit 105 may notify whether a current measurement site is proper to a measurer via speech or display depending on a degree of flatness of the thus-measured amount of measurement.

There has been described in the above explanation the case in which the analysis unit 105 calculates the amount of in vivo component and the like by multiple regression analysis based on the extended Lambert-Beer Law, but the calculation method used by the analysis unit 105 for the analysis processing is not limited to the above example, and a well-known analysis method such as simulation using the Monte Carlo method may be used, for example.

The analysis unit 105 according to the present embodiment has been described above in detail with reference to FIG. 5 to FIG. 7.

[Storage Unit 107]

Returning to FIG. 2, the storage unit 107 provided in the measurement device 10 according to the present embodiment will be described.

The storage unit 107 is realized by the RAM, a storage device, or the like provided in the measurement device 10 according to the present embodiment. The storage unit 107 stores therein data on photoabsorption spectra used for the analysis processing in the analysis unit 105, a look-up table of various databases, and the like. The storage unit 107 may store therein measurement data measured by the measurement unit 101 according to the present embodiment, various programs or parameters or items of data used for the processing performed by the control unit 103 or the analysis unit 105 according to the present embodiment, and the like. The storage unit 107 can store, in addition to the above data, various parameters, processing progresses, and the like which need to be stored for any processing of the measurement device 10, as needed. Each processing unit such as the measurement unit 101, the control unit 103 or the analysis unit 105 can freely access the storage unit 107 and can write or read data in or from the storage unit 107.

The structure of the measurement device 10 according to the present embodiment has been described above in detail with reference to FIG. 2 to FIG. 7.

With the measurement device 10 according to the present embodiment as described above, the amount of in vivo component is analyzed based on the amount of light attenuated depending on an optical distance from the light source, and thus the in vivo component which can cause a variation in optical model (skin structure model) can be accurately measured.

The control unit 103 and the analysis unit 105 according to the present embodiment may be part of the measurement device 10 according to the present embodiment, or may be realized by an external device such as computer connected to the measurement device 10. Measurement data generated by the measurement unit 101 is stored in a removable storage medium and the storage medium is removed from the measurement device 10 to be connected to other device having the analysis unit 105, and thus the measurement data may be analyzed.

A well-known technique used for an ultrasonic diagnosis device may be applied to the measurement unit 101 according to the present embodiment in order to acquire only an analysis result for a thickness of the dermic layer and a thickness of the fat layer by use of the measurement device 10 according to the present embodiment.

Heretofore, an example of the functions of the measurement device 10 according to the present embodiment has been shown. Each of the structural elements described above other than measurement unit 101 may be configured using a general-purpose material or a general-purpose circuit, or may be configured from hardware dedicated to the function of each structural element. Also, a CPU or the like may perform all the functions of the structural elements. Accordingly, the configuration to be used can be changed as appropriate according to the technical level at the time of carrying out the present embodiment.

Additionally, a computer program for realizing each function of control unit and analysis unit according to the present embodiment as described above and a computer program for controlling the control unit and analysis unit according to the present embodiment as described above can be created, and the computer program can be implemented in a personal computer or the like. A recording medium in which such computer program is stored and which can be read by a computer can also be provided. The recording medium is a magnetic disk, an optical disk, a magneto-optical disk, a flash memory, or the like, for example. Also, the computer program may be distributed via a network, for example, without using a recording medium.

<Variants>

[First Variant]

An in vivo component which can cause a variation in optical model (skin structure model) can be accurately measured by use of the measurement device 10 according to the present embodiment described above. Measurement data measured by a different body substance measurement device from the measurement device 10 can be corrected by use of the amount of in vivo component or an attenuation curve acquired by the measurement device 10. Variants of the measurement device 10 according to the present embodiment will be described below in detail with reference to FIG. 8 and FIG. 9.

Figure 8:
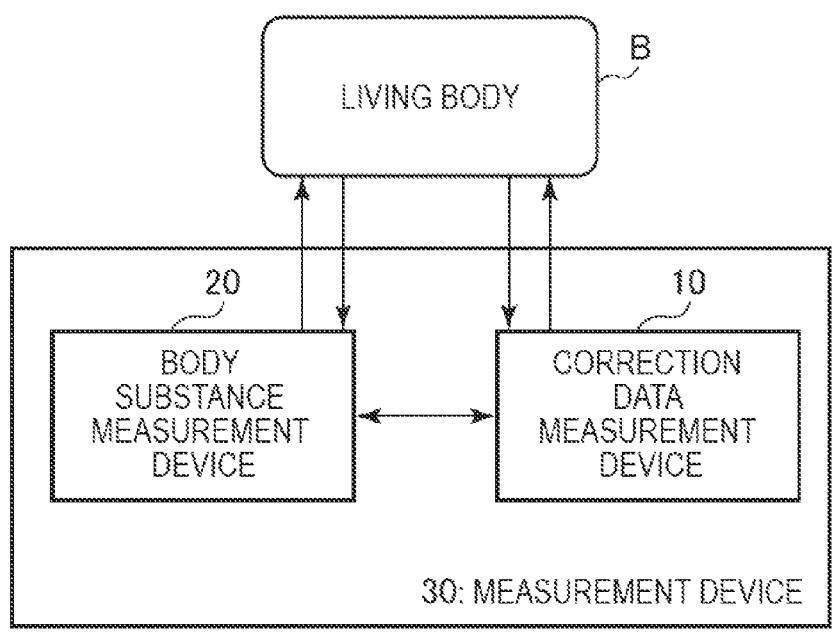
FIG. 8 is a block diagram illustrating a variant of the measurement device according to the embodiment.

In a measurement device 30 according to the present variant, as illustrated in FIG. 8, the measurement device 10 previously described is used as a correction data measurement device 10 for measuring correction data, and measurement data measured by an additionally-provided body substance measurement device 20 is corrected by the amount of in vivo component, an attenuation curve, or the like calculated by the correction data measurement device 10.

Herein, the correction data measurement device 10 according to the present variant has the same structure as the measurement device 10 previously described and obtains the same effects, and thus a detailed explanation thereof will be omitted below.

The body substance measurement device 20 is directed for measuring the abundance of body substance different from an in vivo component measured by the correction data measurement device 10 with various optical methods. A body fluid component or blood component of interest in terms of health-care or the like of a person to be measured, such as glucose, albumin, cholesterol or AGEs (Advanced Glycation Endproducts), is measured by the body substance measurement device 20. A well-known measurement technique can be used as needed for the method for measuring a body substance by the body substance measurement device 20. For example, the body substance measurement device 20 may measure a body substance by use of various spectroscopic methods such as Raman spectroscopy, near-infrared spectroscopy and ultraviolet excitation fluorescence spectroscopy, or may measure a body substance by irradiating an electromagnetic wave such as millimeter wave on a living body to analyze the amount of electromagnetic wave returning from the living body or to measure a change in refractive index.

Figure 9:
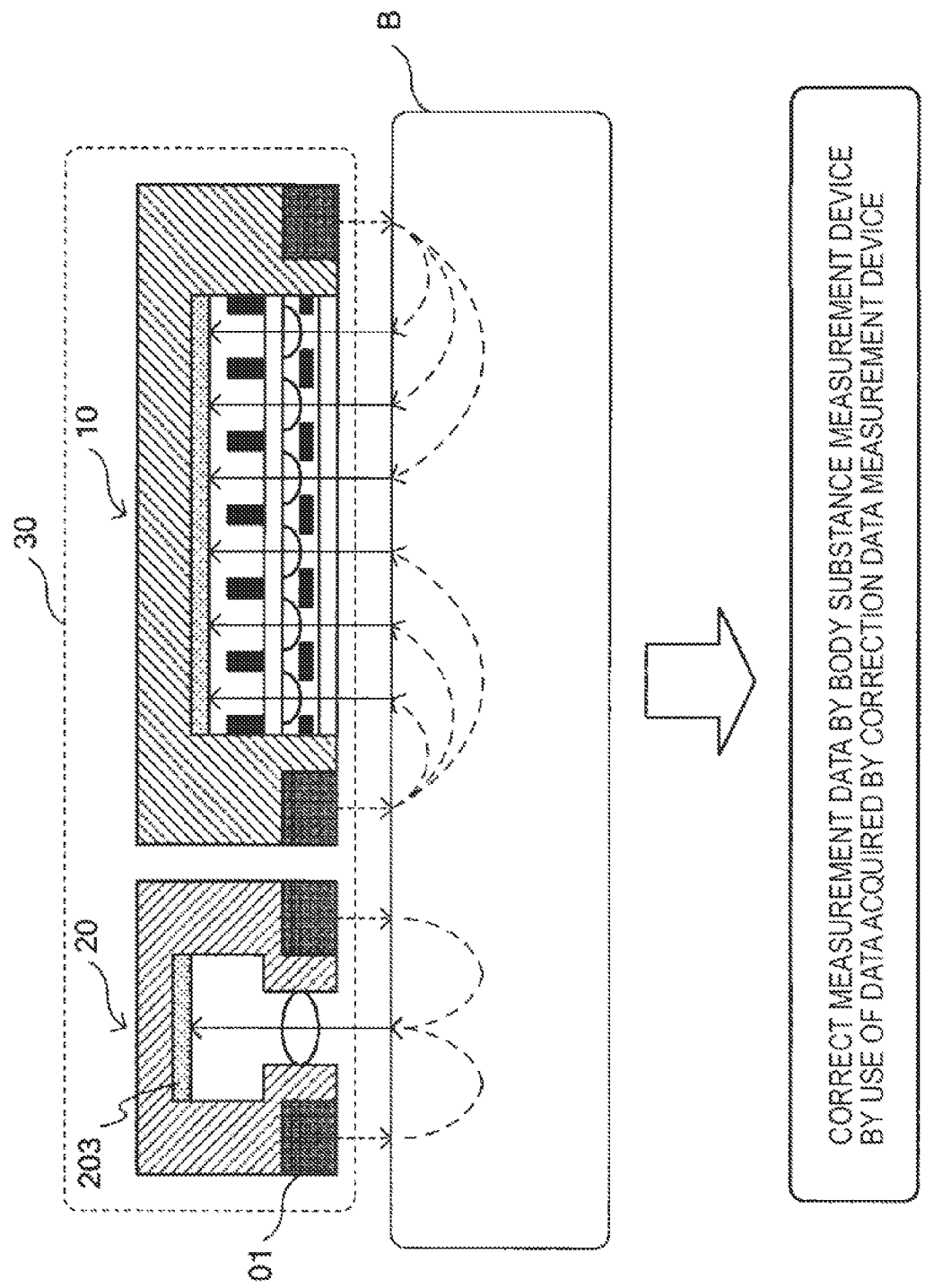
FIG. 9 is an explanatory diagram illustrating an exemplary measurement device according to the variant.

The body substance measurement device 20 measures the abundance of body substance of interest by emitting light with a predetermined wavelength from a light source 201 toward the living body B and detecting transmitted light passing through the living body B by a sensor 203 as illustrated in FIG. 9, for example.

A measurement of an in vivo component by the correction data measurement device 10 and a measurement of a body substance by the body substance measurement device 20 are preferably made at different timings, and measurement light from the light source 201 is preferably irradiated toward the living body B at a different timing from measurement light from the light source 101.

The measurement device 30 according to the present variant corrects (calibrates) measurement data measured by the body substance measurement device 20 by use of the amounts of various in vivo components measured by the correction data measurement device 10, or scattering/diffusion characteristics (or attenuation curve) in the living body. The measurement data correction processing may be performed by the analysis unit 105 provided in the correction data measurement device 10, or may be performed by a control unit or analysis unit (not illustrated) provided in the body substance measurement device 20.

More specifically, the analysis unit 105 or the body substance measurement device 20 corrects an effect (such as attenuation of an intensity of a detected light) caused by light from the light source 201 in the body substance measurement device 20 absorbed or scattered by the skin structure by use of the skin structure model analyzed by the correction data measurement device 10 (such as the amount of in vivo component, a thickness of the layer structure and an attenuation curve). Thereby, a model variation of multivariate analysis made in the body substance measurement device 20 can be corrected, thereby improving deterioration in accuracy of the multivariate analysis made in the body substance measurement device 20 and accurately measuring a body substance.

The correction processing (calibration processing) is preferably performed each time a measurement is made by the body substance measurement device 20. A personal difference or temporal change is directly measured by the correction data measurement device 10, and thus calibration by the body substance measurement device 20 with an invasive measure such as blood withdrawal is not required, thereby enhancing user's convenience.

The examples in FIG. 8 and FIG. 9 illustrate a case in which the correction data measurement device 10 and the body substance measurement device 20 are separately mounted, but the correction data measurement device 10 and the body substance measurement device 20 may be integrally formed within the same casing.

[Second Variant]

The measurement device 10 according to the present embodiment may function as the body substance measurement device 20 according to the first variant. That is, the multi-tap sensor provided in the measurement device 10 according to the present embodiment may perform the measurement processing and the analysis processing for an in vivo component with the above-described method, and may perform a processing of measuring a different body substance from an in vivo component.

For example, there will be assumed a case in which AGEs (Advanced Glycation Endproducts) are quantified by exciting the AGEs present in the skin by an ultraviolet ray and detecting fluorescence emitted from the AGEs. A sensitivity of the sensor 131 found in this case is sufficient even with a silicon sensor such as CCD or CMOS, and thus the measurement device 10 according to the present embodiment may be used as the body substance measurement device 20 even with a measurement method for detecting fluorescence. In this case, an ultraviolet light source capable of emitting an ultraviolet ray as an excitation light, and light sources for measuring in vivo components (such as light sources with 568 nm, 660 nm and 890 nm for quantifying melanin, and light sources with 940 nm, 950 nm and 970 nm for quantifying fat or water) are used for the light source 111 provided in the measurement device 10. Additionally, the control unit 103 emits the light sources in a time division manner thereby to make measurements of components without mutual interferences.

As with a RGB camera, pixels only for ultraviolet ray (for example, a transmission property of the B pixel is extended to an ultraviolet band) and pixels for measuring in vivo components are arranged in a 2D arrangement so that the ultraviolet light source and the light sources for measuring in vivo components are emitted at the same time thereby to make respective measurements.

When glucose as a body substance is measured in terms of a light scattering coefficient of glucose, the light scattering coefficient of glucose can be measured by use of light with a wavelength of visible light band to 1000 nm. Therefore, measurement light for measuring an in vivo component and measurement light for measuring glucose are emitted in a time division manner, thereby measuring the in vivo component and glucose with one sensor 131.

In any of the above cases, a measurement result of a different body substance from an in vivo component can be corrected by use of a measurement result of the in vivo component.

As still another variant, a 2D sensor is used as the sensor 131 to form a spectroscope using prism, thereby measuring a wavelength band in one dimension of the 2D sensor and measuring a change along with a measurement position in the other dimension thereof. Therefore, 1D information on the skin is used for measuring a depth of body fat or dermic layer, thereby achieving the functions according to the present embodiment.

The variants of the measurement device and the measurement method according to the present embodiment have been described above.

(Hardware Configuration)

Figure 10:
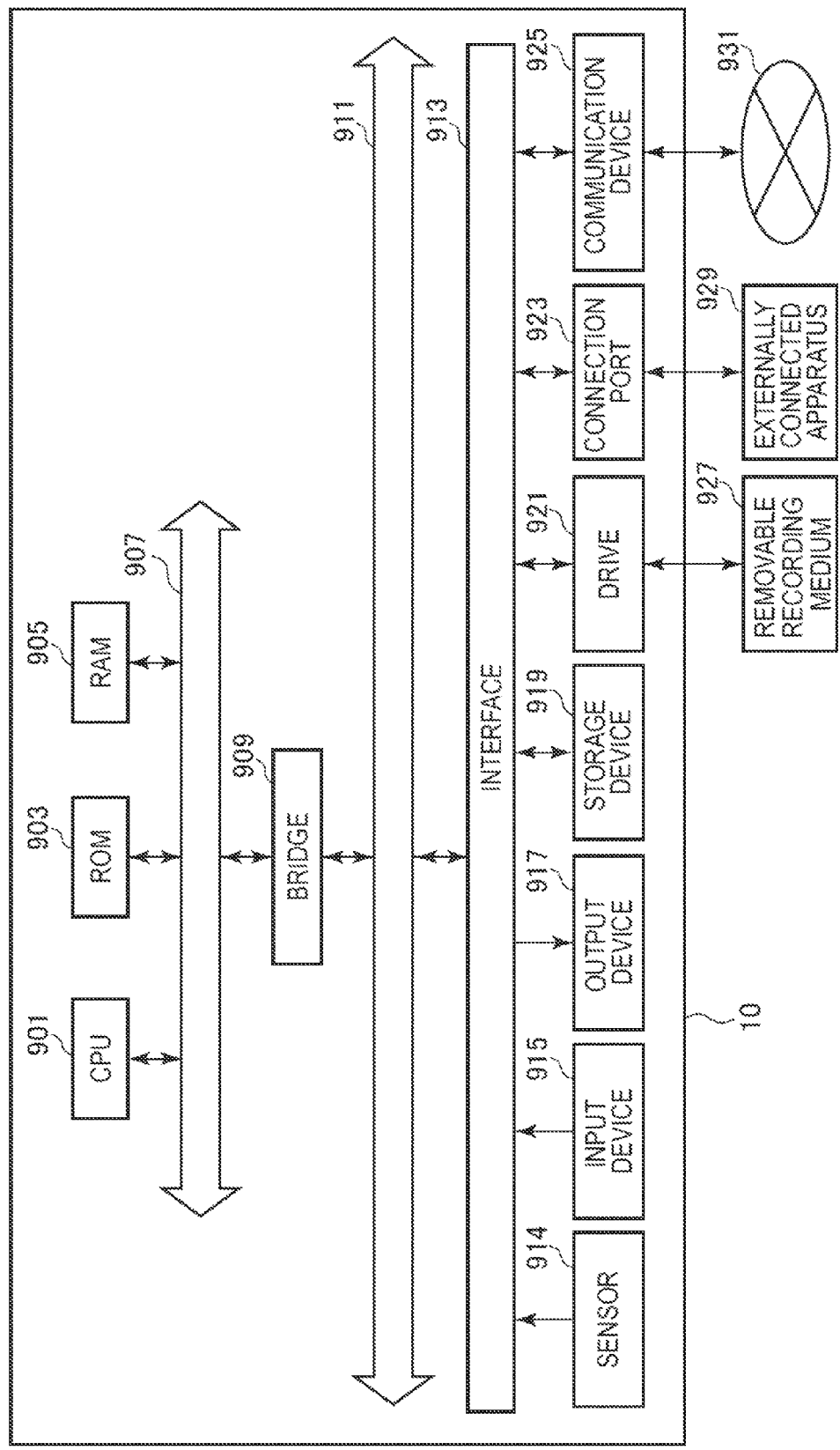
FIG. 10 is a block diagram illustrating an exemplary hardware structure of the measurement device according to the embodiment of the present disclosure.

Next, the hardware configuration of the measurement device 10 according to the embodiment of the present disclosure will be described in detail with reference to FIG. 10. FIG. 10 is a block diagram for illustrating the hardware configuration of the measurement device 10 according to the embodiment of the present disclosure.

The measurement device 10 mainly includes a CPU 901, a ROM 903, and a RAM 905. Furthermore, the measurement device 10 also includes a host bus 907, a bridge 909, an external bus 911, an interface 913, a sensor 914, an input device 915, an output device 917, a storage device 919, a drive 921, a connection port 923, and a communication device 925.

The CPU 901 serves as an arithmetic processing apparatus and a control device, and controls the overall operation or a part of the operation of the measurement device 10 according to various programs recorded in the ROM 903, the RAM 905, the storage device 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like.

The host bus 907 is connected to the external bus 911 such as a PCI (Peripheral Component Interconnect/Interface) bus via the bridge 909.

The sensor 914 is detecting means for detecting biological information unique to a user or various types of information to be used to acquire such biological information. This sensor 914 includes, for example, various imaging devices such as a CCD (Charge Coupled Device) or a CMOS (Complementary Metal Oxide Semiconductor) and the like. In addition, the sensor 914 may further have optics such as a lens to be used to image an organism site or a light source and the like. The sensor 914 may also be a microphone and the like for acquiring sound and the like. Note that in addition to those mentioned above, the sensor 914 may also include various measuring instruments such as a thermometer, an illuminance meter, a hygrometer, a speedometer, an accelerometer, and the like.

The input device 915 is an operation means operated by a user, such as a mouse, a keyboard, a touch panel, buttons, a switch and a lever. Also, the input device 915 may be a remote control means (a so-called remote control) using, for example, infrared light or other radio waves, or may be an externally connected apparatus 929 such as a mobile phone or a PDA conforming to the operation of the measurement device 10. Furthermore, the input device 915 generates an input signal based on, for example, information which is input by a user with the above operation means, and is configured from an input control circuit for outputting the input signal to the CPU 901. The user of the measurement device 10 can input various data to the measurement device 10 and can instruct the measurement device 10 to perform processing by operating this input apparatus 915.

The output device 917 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 917 outputs a result obtained by various processing performed by the measurement device 10. More specifically, the display device displays, in the form of texts or images, a result obtained by various processes performed by the measurement device 10. On the other hand, the audio output device converts an audio signal such as reproduced audio data and sound data into an analog signal, and outputs the analog signal.

The storage device 919 is a device for storing data configured as an example of a storage unit of the measurement device 10 and is used to store data. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various data, and various data obtained from the outside.

The drive 921 is a reader/writer for recording medium, and is embedded in the measurement device 10 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray medium. The removable recording medium 927 may be a CompactFlash (CF; registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing devices to directly connect to the measurement device 10. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (High-Definition Multimedia Interface) port, and the like. By the externally connected apparatus 929 connecting to this connection port 923, the measurement device 10 directly obtains various data from the externally connected apparatus 929 and provides various data to the externally connected apparatus 929.

The communication device 925 is a communication interface configured from, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the measurement device 10 according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

The hardware structure of the body substance measurement device 20 according to the embodiment of the present disclosure is the same as the hardware structure of the measurement device 10 according to the embodiment of the present disclosure and obtains the same effects, and thus a detailed explanation thereof will be omitted below.

(Conclusion)

As described above, with the measurement device and the measurement method according to the embodiment of the present disclosure, an in vivo component or the like, which is an inhabitation factor when light passes through a living body, can be accurately measured. Thereby, the characteristics of scattering and attenuation of light propagation (such as optical changes due to melanin, the amount of blood, a thickness of fat and a thickness of the dermic layer) resulting from a person to be measured and a site to be measured can be modeled.

Further, a resultant measurement result is used for other non-invasive optical measurement thereby to estimate a variation in optical model (such as skin structure model), and thus the amount of light reaching the sensor from a target substance in other non-invasive optical measurement can be accurately corrected. Consequently, deterioration in accuracy of multivariate analysis made in other non-invasive optical measurement can be improved, and calibration by the measurement device with other means such as blood withdrawal is not required.

The preferred embodiment of the present disclosure has been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

Additionally, the present technology may also be configured as below.

(1)

A measurement device including:

a light source for emitting measurement light which is used for measuring an in vivo component present in a living body and belongs to a predetermined wavelength band toward the living body;

a detection unit in which a plurality of sensors is regularly arranged in a predetermined arrangement and which detects the measurement light emitted from the light source and passing through the living body with the plurality of sensors; and an analysis unit which analyzes an amount of the in vivo component based on an amount of light attenuated depending on an optical distance from the light source by use of a detection result detected by the detection unit.

(2)

The measurement device according to (1), wherein the analysis unit models subcutaneous tissues of the living body and analyzes the detection result as a linear sum of absorption by the in vivo component of interest, thereby calculating the amount of the in vivo component.

(3)

The measurement device according to (1) or (2), wherein the detection unit detects measurement light passing through the living body by a sensor utilizing a micro lens array in which a plurality of lenses is regularly arranged in a grid shape.

(4)

The measurement device according to any one of (1) to (3), wherein the light source emits plural kinds of the measurement light with mutually different wavelengths toward the living body in a time division manner.

(5)

The measurement device according to any one of (1) to (4), wherein the analysis unit calculates at least any of an amount of any of melanin, blood component, and water as the in vivo component.

(6)

The measurement device according to (5), wherein the analysis unit further calculates at least any of the amount of blood, a thickness of fat, and a thickness of the dermic layer.

(7)

The measurement device according to any one of (1) to (6), further including:

a body substance measurement device for measuring a substance contained in the living body, wherein the body substance measurement device or the analysis unit corrects a measurement result in the body substance measurement device by use of the amount of the in vivo component.

(8)

The measurement device according to (7), wherein the body substance measurement device or the analysis unit performs correction processing per measurement processing in the body substance measurement device.

(9)

The measurement device according to (7) or (8), wherein the body substance measurement device is formed integral with the measurement device.

(10)

A measurement method including:

emitting measurement light which is used for measuring an in vivo component present in a living body and belongs to a predetermined wavelength band toward the living body;

detecting the measurement light passing through the living body with a detection unit in which a plurality of sensors is regularly arranged in a predetermined arrangement; and analyzing an amount of the in vivo component based on an amount of light attenuated depending on an optical distance from a light source of the measurement light by use of a detected detection result.

(11)

A program for causing a computer capable of controlling a measurement device including a light source for emitting measurement light which is used for measuring an in vivo component present in a living body and belongs to a predetermined wavelength band toward the living body, and a detection unit in which a plurality of sensors is regularly arranged in a predetermined arrangement and which detects the measurement light emitted from the light source and passing through the living body with the plurality of sensors to achieve:

a control function of controlling the light source and the detection unit; and an analysis function of analyzing an amount of the in vivo component based on an amount of light attenuated depending on an optical distance from the light source by use of a detection result detected by the detection unit.

(12)

A recording medium recording a program therein, the program causing a computer capable of controlling a measurement device including a light source for emitting measurement light which is used for measuring an in vivo component present in a living body and belongs to a predetermined wavelength band toward the living body, and a detection unit in which a plurality of sensors is regularly arranged in a predetermined arrangement and which detects the measurement light emitted from the light source and passing through the living body with the plurality of sensors to achieve:

a control function of controlling the light source and the detection unit; and an analysis function of analyzing an amount of the in vivo component based on an amount of light attenuated depending on an optical distance from the light source by use of a detection result detected by the detection unit.

(13)

A measurement device including:

a body substance measurement device which measures a substance to be measured contained in a living body;

a light source for emitting measurement light which is used for measuring a different in vivo component from the substance to be measured present in the living body and belongs to a predetermined wavelength band toward the living body;

a detection unit in which a plurality of sensors is regularly arranged in a predetermined arrangement and which detects the measurement light emitted from the light source and passing through the living body with the plurality of sensors; and an analysis unit which analyzes an amount of the in vivo component based on an amount of light attenuated depending on an optical distance from the light source by use of a detection result detected by the detection unit.

(14)

A measurement device including:

a body substance measurement device which measures a substance to be measured contained in a living body;

a light source for emitting measurement light which is used for measuring a different in vivo component from the substance to be measured present in the living body and belongs to a predetermined wavelength band toward the living body;

a detection unit in which a plurality of sensors is regularly arranged in a predetermined arrangement and which detects the measurement light emitted from the light source and passing through the living body with the plurality of sensors; and an analysis unit which analyzes an amount of the in vivo component based on an amount of light attenuated depending on an optical distance from the light source by use of a detection result detected by the detection unit, wherein the body substance measurement device or the analysis unit corrects a measurement result in the body substance measurement device by use of the amount of the in vivo component.

REFERENCE SIGNS LIST 10 measurement device (correction data measurement device)
20 body substance measurement device
101 measurement unit
103 control unit
105 analysis unit
107 storage unit
111 light source
121 transparent substrate
123 first light shield
125 micro lens array
127 micro lens
129 second light shield
131 sensor
201 light source
203 sensor

The invention claimed is:

1. A measurement device comprising:
a body substance measurement device which measures a substance to be measured contained in a living body, the body substance measurement device having a first light source to emit light and a sensor to detect the light emitted from the first light source passing through the living body; and
a correction data measurement device having
(i) a second light source for emitting measurement light which is used for measuring a different in vivo component from the substance to be measured present in the living body and belongs to a predetermined wavelength band toward the living body;
(ii) a detection unit in which a plurality of sensors is regularly arranged in a predetermined arrangement and which detects the measurement light emitted from the second light source and passing through the living body with the plurality of sensors; and
(iii) an analysis unit which analyzes an amount of the in vivo component based on an amount of light attenuated depending on an optical distance from the second light source by use of a detection result detected by the detection unit,
the body substance measurement device is configured to cause the first light source to emit the light at a first timing and the correction data measurement device is configured to cause the second light source to emit the measurement light at a second timing, in which the first timing is different from the second timing,
wherein the analysis performed by the analysis unit comprises formulating a rate of light absorption by the in vivo component for light propagating inside the living body based on at least a plurality of layers of the living body and, for each layer, an indication of a number of substances in the layer.

2. The measurement device according to claim 1,
wherein the analysis unit models subcutaneous tissues of the living body and analyzes the detection result as a linear sum of absorption by the in vivo component of interest, thereby calculating the amount of the in vivo component.

3. The measurement device according to claim 2,
wherein the detection unit detects measurement light passing through the living body by a second sensor utilizing a micro lens array in which a plurality of lenses is regularly arranged in a grid shape.

4. The measurement device according to claim 1,
wherein the analysis unit calculates at least any of an amount of any of melanin, blood component, and water as the in vivo component.

5. The measurement device according to claim 4,
wherein the analysis unit further calculates at least any of the amount of blood, a thickness of fat, and a thickness of the dermic layer.

6. The measurement device according to claim 1, wherein the body substance measurement device or the analysis unit corrects a measurement result in the body substance measurement device by use of the amount of the in vivo component.

7. A measurement method for use with a measurement device having a body substance measurement device and a correction data measurement device, said method comprising:
measuring, by use of the body substance measurement device, a substance to be measured contained in a living body by emitting light from a first light source of the body substance measurement device and detecting the light emitted from the first light source passing through the living body by a sensor of the body substance measurement device; and
using the correction data measurement device to
(i) cause a second light source to emit measurement light for measuring a different in vivo component from the substance to be measured present in the living body and having a predetermined wavelength band toward the living body;
(ii) detect the measurement light emitted from the second light source and passing through the living body with a plurality of sensors regularly arranged in a predetermined arrangement; and
(iii) analyze an amount of the in vivo component based on an amount of light attenuated depending on an optical distance from the second light source by use of a detection result detected by the detection unit,
in which the first light source is caused to emit the light at a first timing and the second light source is caused to emit the measurement light at a second timing, in which the first timing is different from the second timing,
wherein using the correction data measurement device to analyze comprises formulating a rate of light absorption by the in vivo component for light propagating inside the living body based on at least a plurality of layers of the living body and, for each layer, an indication of a number of substances in the layer.

8. A non-transitory computer readable storage medium having stored thereon a program for causing a computer to control a measurement device having a body substance measurement device and a correction data measurement device to perform a method, said method comprising:
measuring, by use of the body substance measurement device, a substance to be measured contained in a living body by emitting light from a first light source of the body substance measurement device and detecting the light emitted from the first light source passing through the living body by a sensor of the body substance measurement device; and using the correction data measurement device to
(i) cause a second light source to emit measurement light for measuring a different in vivo component from the substance to be measured present in the living body and having a predetermined wavelength band toward the living body;
(ii) detect the measurement light emitted from the second light source and passing through the living body with a plurality of sensors regularly arranged in a predetermined arrangement; and
(iii) analyze an amount of the in vivo component based on an amount of light attenuated depending on an optical distance from the second light source by use of a detection result detected by the detection unit,
in which the first light source is caused to emit the light at a first timing and the second light source is caused to emit the measurement light at a second timing, in which the first timing is different from the second timing,
wherein using the correction data measurement device to analyze comprises formulating a rate of light absorption by the in vivo component for light propagating inside the living body based on at least a plurality of layers of the living body and, for each layer, an indication of a number of substances in the layer.

\* \* \* \* \*